US 6,443,978 B1

(12) United States Patent
Zharov

(10) Patent No.: US 6,443,978 B1
(45) Date of Patent: Sep. 3, 2002

(54) PHOTOMATRIX DEVICE

(75) Inventor: Vladimir Pavlovich Zharov, Moscow (RU)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/646,824
(22) PCT Filed: Apr. 9, 1999
(86) PCT No.: PCT/RU99/00111
§ 371 (c)(1),
(2), (4) Date: Sep. 22, 2000
(87) PCT Pub. No.: WO99/52597
PCT Pub. Date: Oct. 21, 1999

(51) Int. Cl.⁷ .............................................. A61N 5/006
(52) U.S. Cl. ............................ 607/91; 607/88; 607/89; 606/2; 606/13
(58) Field of Search ......................... 607/88–91, 93–95; 606/3, 9–11; 128/898

(56) References Cited

U.S. PATENT DOCUMENTS

| 4,239,040 A | 12/1980 | Hosoya et al. |
| 4,930,504 A | 6/1990 | Diamontopoulos et al. |
| 5,259,380 A | 11/1993 | Mendes et al. |

(List continued on next page.)

FOREIGN PATENT DOCUMENTS

| GB | 2212010 | 7/1989 |
| RU | 2045972 | 10/1995 |
| RU | 2055609 | 3/1996 |
| RU | 2072880 | 2/1997 |
| RU | 2145247 | 2/2000 |

OTHER PUBLICATIONS

Illarionov, V.E., Fundamentals of Laser Therapy, Moscow, Respect, 1992, pp. 26, 31, 71–80, 40–45.
Drollette, D., Can Light Hasten Healing in Space?, Biophotonics International, Sep./Oct. 2000, pp. 46–49.
Zharov, V., et al., Laser Combined Medical Technologies from Russia, Journal of Laser Applications, Apr. 1999, pp. 80–90.
Online website, www.palmed.com, Palomar Medical Technologies, Inc., 6 pages concerning Palomar SLP1000 (TM), Dec. 12, 2000.
Internet website, http://www.oirf.com, Occidental Institute Research Foundation, Penticton, British Columbia, Canada, Feb. 22, 2001, 6 pp.

(List continued on next page.)

Primary Examiner—Linda C. M. Dvorak
Assistant Examiner—Ahmed Farah
(74) Attorney, Agent, or Firm—Ray F. Cox, Jr.

(57) ABSTRACT

A device for the physiotherapeutic irradiation of spatially extensive pathologies by light with the help of a matrix of the sources of optical radiation such as lasers or light diodes placed on the surface of a substrate whose shape is adequate to the shape of the zone of pathology is disclosed. In addition, the device contains stops and a holder to fix the substrate against the bioobject. Additional modules are provided to adjust the temperature, pressure, gas composition over the pathological area. As a source of radiation, chemical reactions accompanied by the luminescence of the products of reaction are suggested. The power supply unit can be autonomous with remote feeding through pulse magnetic field. A supplementary hood optically transparent is provided to localize the pathology as well as the strips that scatter the radiation to get a more uniform bioobject's exposure. Application: light-therapy to treat various extensive pathologies on the bioobject's surface including dermatology, cosmetology; the treatment of traumas, bruises, oedemas, varicose veins, blood therapy, treatment of infectious processes.

80 Claims, 7 Drawing Sheets

U.S. PATENT DOCUMENTS

Figure 3:
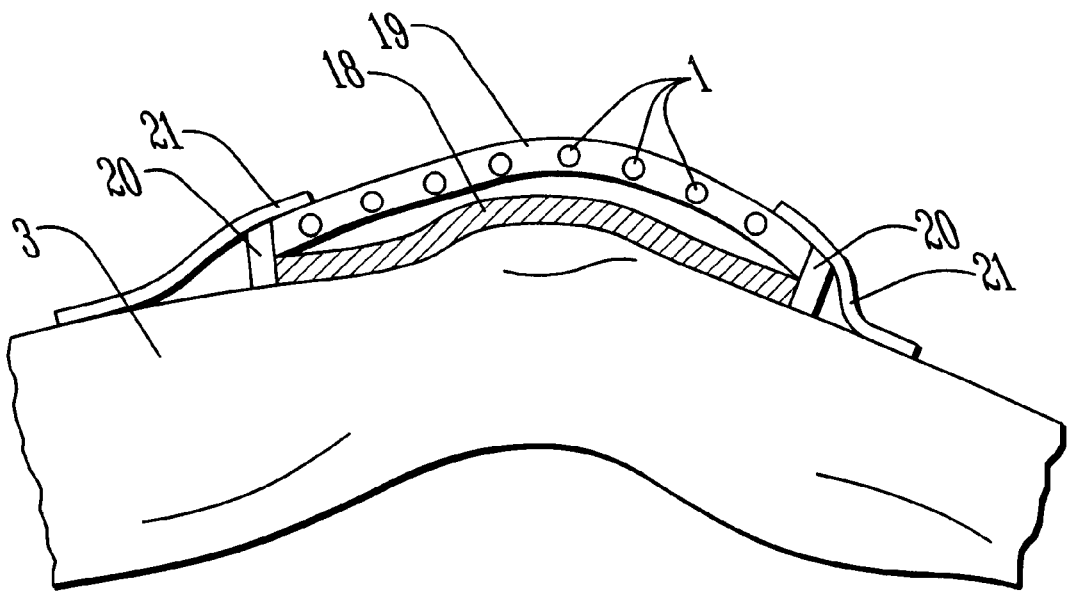

| | | | | |
|---|---|---|---|---|
| 5,278,432 A | | 1/1994 | Ignatius et al. | |
| 5,339,223 A | * | 8/1994 | Kremenchugsky et al. | ... 362/32 |
| 5,358,503 A | | 10/1994 | Bertwell et al. | |
| 5,445,608 A | | 8/1995 | Chen et al. | |
| 5,489,279 A | | 2/1996 | Meserol | |
| 5,549,660 A | | 8/1996 | Mendes et al. | |
| 5,571,151 A | | 11/1996 | Chen et al. | |
| 5,616,140 A | * | 4/1997 | Prescott | |
| 5,660,461 A | | 8/1997 | Ignatius et al. | |
| 5,698,866 A | | 12/1997 | Doiron et al. | |
| 5,728,090 A | | 3/1998 | Martin et al. | |
| 5,766,222 A | | 6/1998 | Petit | |
| 5,766,234 A | | 6/1998 | Chen et al. | |
| 5,845,640 A | | 12/1998 | Lawandy | |
| 5,913,883 A | * | 6/1999 | Alexander et al. | 607/88 |
| 6,045,575 A | * | 4/2000 | Rosen et al. | 607/88 |
| 6,096,066 A | * | 8/2000 | Chen et al. | 607/88 |
| 6,290,713 B1 | * | 9/2001 | Russell | 607/88 |

OTHER PUBLICATIONS

Internet website, http://www.laserhealthsystems.com, Laser Therapeutics, Inc., Hyannisport, Massachusetts, Feb. 22, 2001, 2 pp.

Internet website, http://www.thermotex.com, Thermotex Therapy Systems Ltd., Calgary, Alberta, Canada, Feb. 22, 2001, 2 pp.

Internet website, http://www.ultra–lite.com, Ultra–Lite Therapy, Lynchburg, Virginia, Feb. 22, 2001, 3 pp.

Internet website, http://www.therapy.com, Equi–Lite, Inc., Denver, Colorado, Feb. 22, 2001, 1 p.

Internet website, http://www.painxequine.com, Performance Horse Therapy, Keyes, Oklahoma, 3 pp.

Internet website, http://www.painx2000equinetherapy.com, Performance Horse Therapy, Joliet, Montana, Feb. 22, 2001, 4 pp.

Internet website, http://www.bioscanlight.com, BioScan, Inc., New Mexico, Feb. 22, 2001, 6 pp.

* cited by examiner

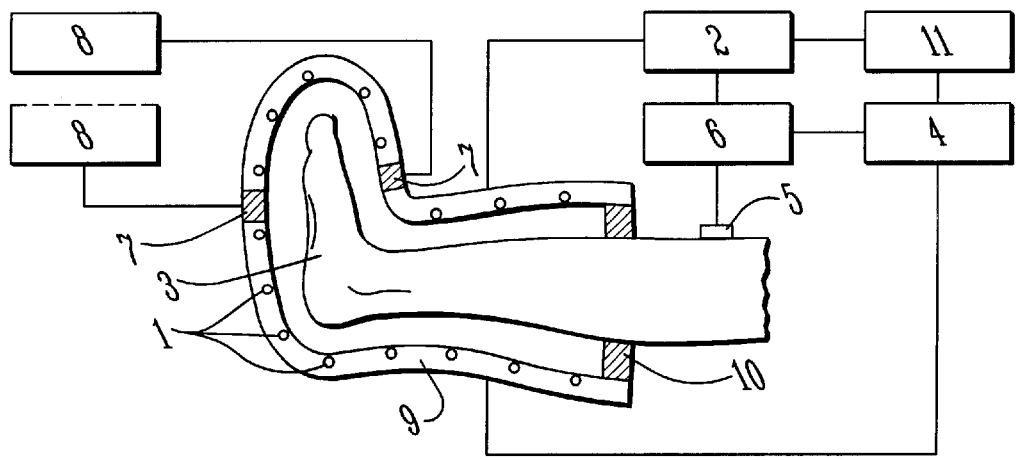
FIG.1
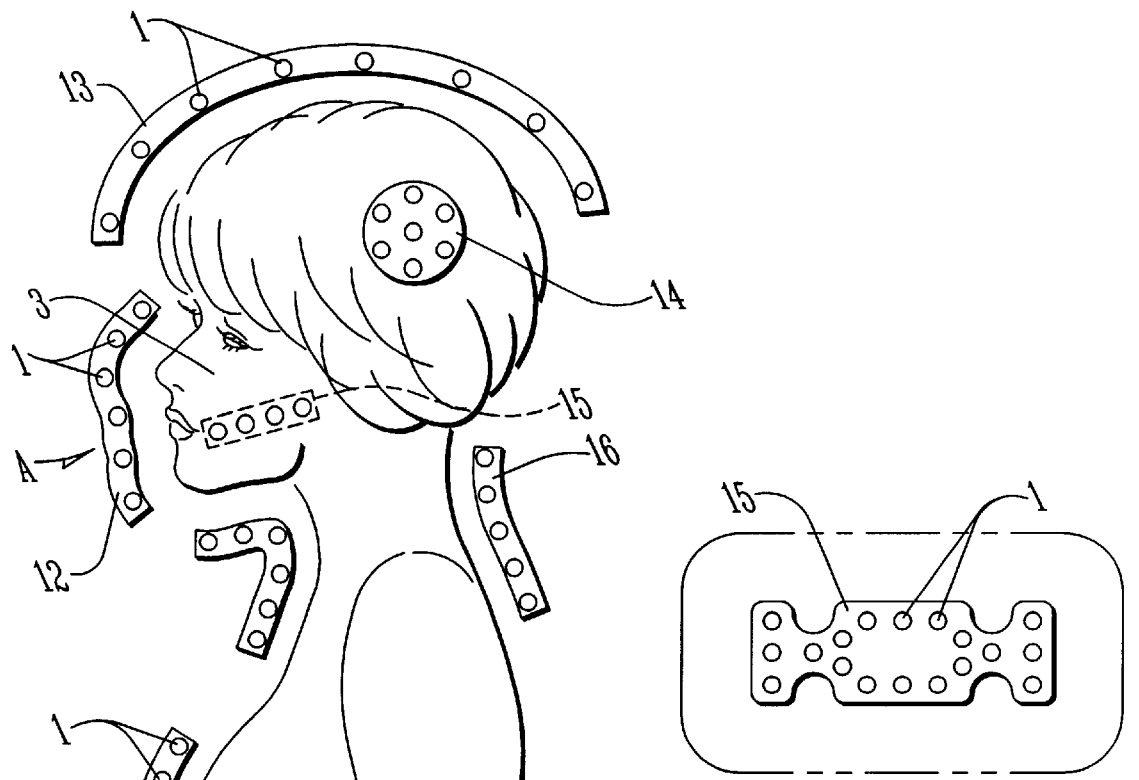
FIG.2
FIG.2A

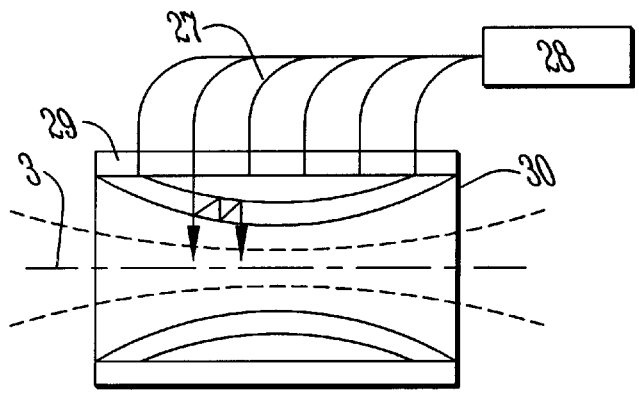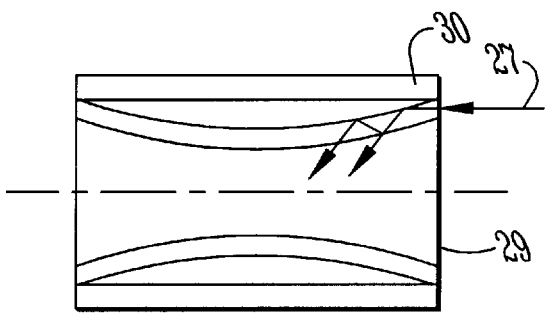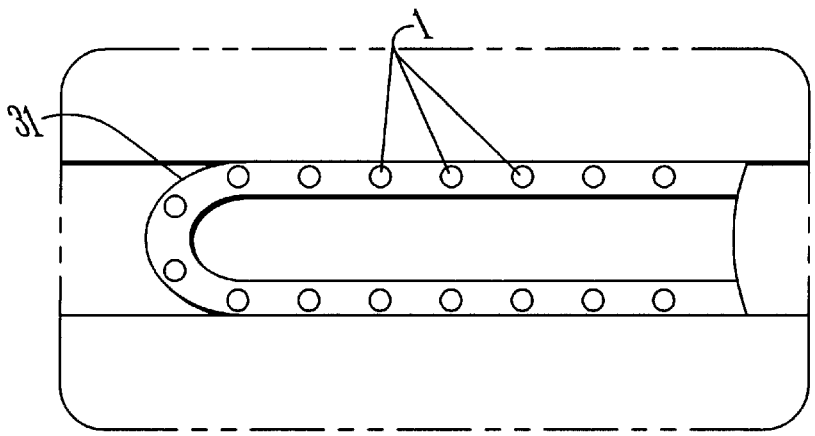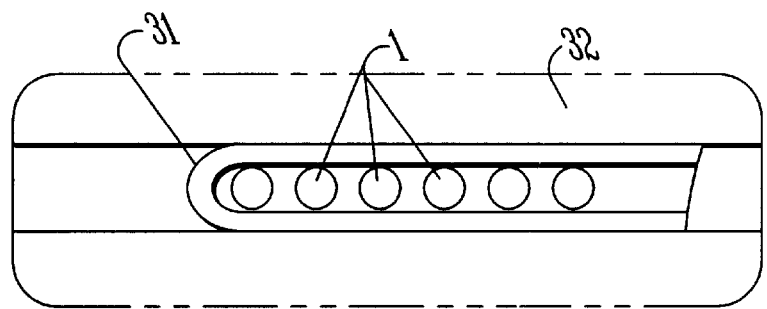

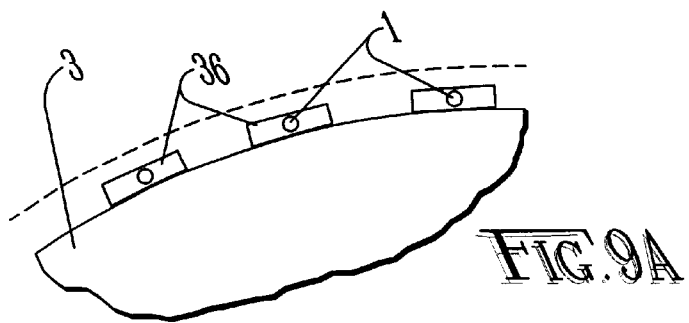
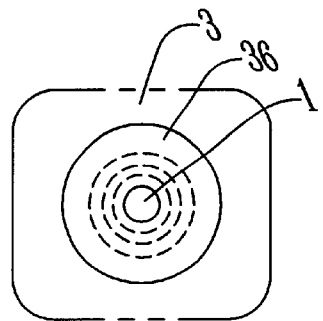
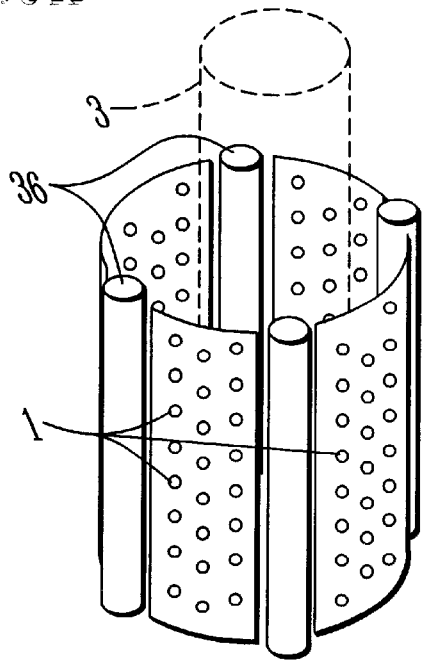
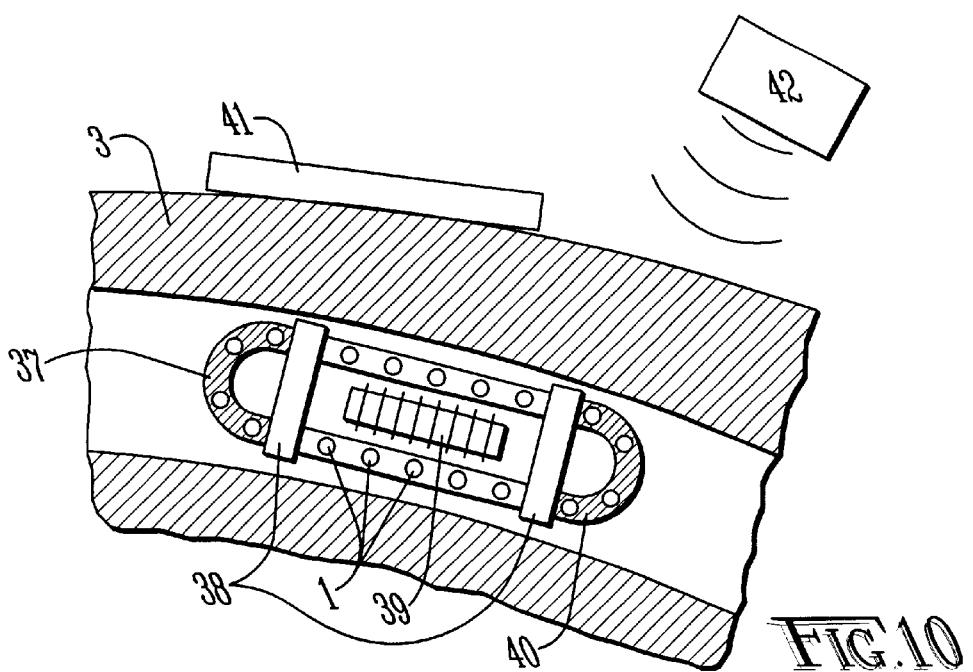

PHOTOMATRIX DEVICE

TECHNICAL FIELD

This invention concerns medicine and biology, in particular, it concerns physiotherapy and photobiology and it deals with the therapeutic influence of light on various human being's organs, micro-organisms and plants in combination with other kinds of energy, including magnetic field, electrostimulation, mechanical therapy, vacuum-therapy, etc.

PREVIOUS LEVEL OF TECHNOLOGY

A device for light-therapeutic influence on different human being's areas is known; it consists of the sources of optical radiation, for example, such as lasers or light diodes coupled with a power supply unit and a timer [Illarionov V.E. Fundamentals of laser therapy, Moscow, Respect, 1992, pp. 26, 31, 71–80]. Sources of radiation are placed separately or installed into anglepoised heads or connected with light fibers, through which the radiation is directed onto the bioobject. The disadvantage of such devices is the difficulty in creating the uniform light exposure over extensive pathological zones on the human being's body, especially when these zones have complex spatial geometry.

The closest device, in technical terms, is a combined therapeutic device, which consists of several narrow-band sources in form of light diodes with the radiation wavelengths varying in the spectrum range from 0.25 $\mu$m to 2 $\mu$m [1]. The sources of radiation can operate either in a continuous mode or in a pulse one with a wide range of frequencies and pulse profiles. The sources of radiation are usually placed at the butt-end parts of anglepoised hands, which can be fixed against the shell of a power supply unit with the help of special holders.

The drawbacks of these device are the impossibility to irradiate extensive pathological zones when they are located, for instance, on different sides of the bioobject, which is typical, in particular, for burns, oedemas or dermatological pathologies that involve all sides of a limb; difficulty in selective irradiation of a surface with complex geometry in accordance with the given pattern of irradiation, for example, elbow and knee bents, the upper side of the head, areas of the alimentary tract, sex organs, etc. with the simultaneous exception of neighbouring areas from the process of irradiation; the impossibility of establishing a required distance between the sources of radiation and bioobject along the whole pathological zone, particularly, to avoid the danger of potential touching a wounded or burnt surface by the sources at involuntary movements of the patient; excessive locality and low dose of influence with respect to the whole pathology in photodynamic therapy of voluminous tumours or in the above-skin irradiation of blood.

DISCLOSURE OF THE INVENTION

In order to exclude the shortcomings mentioned, i.e., to increase the effectiveness of light therapy when treating extensive pathological zones with a complex geometry, the device is equipped with the sources of radiation with a singular spectrum range or various spectrum ranges which are connected with a control unit, a power supply unit and supplementary physiotherapeutic modules (ultrasonic, vacuum, magnetic, electric and other kinds of therapy) placed outside, in particular, on a substrate whose shape is similar to the shape of the spatially extensive pathological zone. Indicatrixes of radiation for each source and their position in space around the bioobject are oriented so as to provide the required distribution, for example, a uniform light exposure within the area of interest. Wavelengths of the sources are chosen on the basis of concurring the absorption wavelengths of biomolecules of both exogenous and endogenous origins.

The sources of radiation (emitters) in the case of a relatively smooth change of the surface relief are placed uniformly on the substrate. Their number N, the distance between them d and the power for each of them P can approximately be determined from the system of interconnected expressions:

$$P \approx \frac{I\pi R^2}{k}; \tag{1}$$

$$d \leq \frac{2R}{k}; \tag{2}$$

$$N \geq \frac{IS}{P\tau}, \tag{3}$$

where I—the intensity of radiation on the bioobject's surface with the pathological zone square S; R—the mean radius of the light spot on the bioobject produced by a single source of radiation that is determined through the equation R=h·tg $\alpha$, where h—the average distance between the surface of the substrate and the bioobject; $\alpha$—the half-angle of divergence of radiation from the source; $\tau$—losses of radiation in optical systems ($0 \leq \tau \leq 1$); k—the ratio that takes into consideration the degree of overlapping the light beams on the bioobject's surface ($1k \leq N$).

In order to introduce the average distance h between the object and the source of radiation and to avoid their touching, additional stops are placed between the source of radiation and bioobject. For instance, these stops can be made in form of spring elements connected with the substrate at one side and with flexible rings, which grasp the bioobject (for example, a limb), at the other side. To get the best usage of the radiation scattered or reflected from the bioobject, the surface of the substrate between the sources of radiation is made mirror-like. In order to fix the substrate against the bioobject, a holder in form of, for instance, adhesive tape is introduced. A commutation unit, coupled with the control unit, and other physiotherapeutic modules as well as the biological sensors of feedback connected with the commutation unit are introduced additionally, which provides the switching of the sources with different spectrum ranges and supplementary physiotherapeutic modules in accordance with a program given, for example, it can provide their separate or simultaneous operation.

Apart from that, the substrate can be furnished with side flanges, which have elastic edges bordering on the bioobject's surface, to provide the air-tightness of the space over the pathological area, with additional modules connected with the corresponding control units being installed into the substrate to regulate the temperature, pressure and gas composition over the pathological area as well as to bring various medicinal and other substances, for instance, magnetic fluids and sprays.

Moreover, a hood transparent for the radiation is introduced between the surfaces of the substrate and bioobject, with its edges adjoining the bioobject's surface, into which the physiotherapeutic modules enumerated above are installed.

Furthermore, a flexible elastic strip grasping the pathological area tightly is introduced between the surfaces of the substrate and bioobject; the strip is suffused with a medicinal compound and is transparent for the optical-range radiation employed.

The light sources can be made in form of distant ends of light-guides connected with the corresponding sources of radiation, in particular, with lasers installed into the substrate, with the semi-mirror-like diffusive strip following the bioobject's shape and being placed between the surfaces of the substrate and bioobject. A required distribution of radiation, including a uniform one, over a large surface can also be achieved with the help of the system of splitting mirrors.

The control and commutation units together with the autonomous power supply unit can be placed immediately on the substrate, with the power supply unit being made either as a one-time operation unit using the packet of miniature batteries or as a re-usable operation unit at the expense of using re-chargeable batteries. Remote power supply is realised by inductive coil coupled with the sources of radiation and additional physiotherapeutic modules, in particular, with electrodes for an electrostimulator, and an external source of pulse electromagnetic field with the following parameters: the pulse width is about $10^{-6}$–$10^{-2}$ sec, the tension of the magnetic field is $10^{-3}$–10 Tesla, the frequency of repetition is 1–$10^3$ Hz.

The source of optical radiation can also be made in form of a concavity shaped in the substrate having optical windows filled with chemical substances, in which the radiation is formed in the course of chemical reactions between separate substances or as a result of non-linear interactions of the radiation from the primary sources of radiation with the substances by means of various physical effects, including the doubling of harmonics, combinational scattering and fluorescence.

In all the modifications of photomatrix systems enumerated above the substrate can be made of rigid materials such as metal, plastic, polymerised substance, glass, ceramics, or other materials. The sources of radiation can be fixed mechanically or with the help of glue. At relatively small caviture of the surface, the substrate can be made as a monolithic integrated chip with hybrid microcristalline light diodes or lasers soldered-in. Given the high density of placing the light diodes and high feeding electric currents, it is necessary to introduce a cooling system on both the working surface of the substrate turned to the bioobject and its external side, for example, with help of micro-fans.

If the spatial geometry is very complex and causes certain difficulties in creating continuous rigid matrix, the latter should be made of separate segments with a flat or nearly flat working surface attached to each other with a rigid or flexible bond. The simplest form of these segments is rectangular and they can be manufactured in form of integrated chips, grasping the pathologic area, for example a limb, uniformly on all sides. The size of separate segments and their shape should trace the relief of the surface.

Using compact and light sources of radiation, for instance, light diodes, it is likely to fix them to a soft flexible substrate such as a piece of medical fabric, gauze, adhesive tape which at wrapping or grasping adopts the shape of the pathological area. A protective transparent substrate or film can be introduced near the sources of radiation to isolate them from the bioobject, which is indispensable for disinfection. Each source of radiation can have its independent optics, for example, positive or negative lenses or diffusive coating, in particular, on the surface of light diodes, which provides the re-distribution of energy of radiation within a wide angle: up to 180°. It is also workable to utilise a common diffusive screen for all the sources.

In the first place in this invention it is suggested to use compact semiconductor hybrid lasers and light diodes emitting within a wide range of spectrum and possessing a broad range of technical parameters. Nevertheless, one can employ compact discharge and luminescent lamps as well as sources operating in the radio-wave range. It is promising to utilise photomatrix systems in photodynamic therapy of both malignant and non-malignant diseases. In order to irradiate extensive oncological tumours, external matrixes with lasers or light diodes can be applied. Modern semiconductor technology allows one to reach the flux from light diodes up to 200 mW/cm$^2$ over the square up to 1,000–2,000 cm$^2$ at the wavelength of absorption for widely known photosensitizers in the range from 0.63 to 0.8 $\mu$m. It is also suggested to densely place light diodes within cylindrical and spherical probes and catheters to use them jointly with endoscopic techniques during irradiation of tumours in the alimentary tract or when puncturing tissues.

Among non-malignant applications of photodynamic therapy, it is suggested to utilise photomatrixes to treat various dermatologic diseases and infectious processes largely due to the bactericidal action of photosensitizers through generating active radicals and singlet oxygen. Since any photosensitizer is able to kill only determine kinds of bacteria, its universality can be increased by means of using photomatrixes with different wavelengths so as to irradiate photosensitizer mixtures with different absorption bands. In order to provide the additional intermingling of the photosensitizer in the solution over the pathological zone, it is suggested to employ an ultrasonic device whose working tip is placed into corresponding solution. Radicals will be formed in the solution in force of the cavitation effect, i.e., one can realise the combined mode of photosonodynamic therapy.

In addition, it is suggested to utilise high-power infrared light diodes (up to 0.5–5 W) that provide the short-term heating of pathologic zones up to 40–41° C. to enhance blood microcirculation, which is healthful at treating arthritis. The heating of bioobject's surface, which is in contact with the photomatrix, can be actualised through heating the photomatrix itself.

Compactness, lightness and flexibility of the photomatrixes allow combining them with other therapeutic techniques, in particular, with apparatuses for magnetic therapy and electrostimulation. This can be reached by means of installing photomatrixes into devices, which generate both continuous and pulse magnetic fields, for instance, solenoids with flat and cylindrical geometry. It is also suggested that photomatrixes be combined with electrostimulators through docking electrodes at the edges of photomatrixes or in form of multi-electrode systems, for example, small metal needles placed between the sources of radiation.

The photomatrixes' shape can be chosen arbitrarily but it should be maximally adapted to the geometry of the pathological area. Particularly, the following shapes have been suggested: in form of a facial mask, glove, gadgets that follow the internal shape of the nose, ear, mouth and other inner concavities; built into transurethral, transrectal catheters, gynaecological probes. Matrixes with the shapes that permit one to uniformly wrap the areas of adipose tissue accumulation, for instance, on the stomach, neck, thighs are also suggested to transform, for example by means of using the photosensitizers, the adipose tissue into soluble compounds that can be eliminated out of the organism easily. The photomatrixes suggested are easy to put into human being's clothes, bed constant wear garment, subjects of household activities (watches, spectacles, bracelets, etc.) to irradiate the body according to a special program so as to regulate his or her mood, to influence the biological rhythms, immune system, blood. It is feasible to locate photomatrixes on the outside part of low-pressure chambers, incubators for new-borns, transparent chambers to conduct photobiological investigations of photosynthesis and agricultural experiments. The usage of infrared sources in so-called windows of transparency for biological tissues allows providing the uniform exposure of some internal organs, particularly, the lungs to treat tuberculosis, the brain to accelerate the production of a number of biological molecules such as serotonin.

Thanks to the features marked above, the device declared is the first to provide the effective treatment of spatially extensive pathological zones, including oedemas, varicose veins, dermatologic and oncologic diseases, extensive infectious and inflammatory processes (ulcers, pus wounds, etc.), it also provides the efficient light-therapy of blood, therapy of yellow jaundice, etc.

The most significant difference is that the shape of the substrate with the sources of radiation traces the shape of the pathological zone irradiated with any configuration and square, which have never previously been achieved. Using this device, it is practicable to uniformly irradiate the whole face, head (cosmetology, dermatology), sex organs (treatment of prostatitis, impotence), elbow and knee joints, woman's breast, limbs including feet and hand fingers, as well as the whole human being's body.

Any sources of radiation can be taken but the most promising ones according to the overall dimensions and economic reasons, as it has been mentioned above, are the semiconductor lasers of a small size and super-miniature light diodes emitting radiation in a spectrum range of 0.25 $\mu$m up to 2–3 $\mu$m. Numerous fundamental investigations have shown that biological action of laser and light diode sources of radiation with a relatively narrow emitting band up to 15–20 nm is practically identical, with the absorption width of basic biostructure components being quite wide: up to 40–60 nm, which allows the utilisation of non-laser sources of radiation in medicine. In the capacity of the sources of radiation with the required spectrum range, the radiation of chemeluminescence caused by the chemical reactions of a number of substances can also be employed. When one uses relatively bulky and cumbersome lasers, it is feasible to employ the standard delivery of radiation towards the bioobject through light-guides. However, in order to irradiate extensive areas, it is requisite to utilise a multi-fibre system, in which separate fibres are gathered in one tight plait and at the end of the plait the fibres are attached to separate areas of the substrate, with a diffusive semi-mirror-like (semi-transparent) strip being introduced to produce a more uniform exposure, which provides the required effect by dint of re-reflecting and scattering the radiation within this strip. The minimum number of sources of radiation is determined in accordance with the expressions (1)–(3) to satisfy the required degree of overlapping the light zones from each source of radiation on the bioobject's surface. To make use of the radiation with better efficiency, in particular, to use the radiation reflected from the bioobject, the working surface of the substrate should be made mirror-like. The beneficial advantage of this invention is the presence of stops, which establish the mean distance between the surfaces of the substrate and bioobject, and a holder that fixes the substrate on the patient's body. In this case there is no necessity for the patient to be immovable during the therapeutic procedure and there is no possibility for the sources of radiation to accidentally touch ulcers, pus wounds or burns, even if the distance between the surface of the substrate and the bioobject is small and if the spatial geometry is complex.

According to the analysis conducted, different physiotherapeutic techniques supplement each other favourably and in combination they can provide a significant treating response. In this invention, this advantage is provided particularly by means of using both light-therapy and electromagnetic therapy. The sources of continuous or pulse magnetic field are placed on the substrate or near it and influence the bioobject sequentially or synchronically with the light radiation, which is set by the commutation unit. In the device depicted, a feedback channel is worked out operating on the basis of various biosensors (acoustic, rheographic, temperature, etc.) that register the corresponding effects of combined influence on the organism and manage the cure process through the commutation unit.

In this device, due to the creation of the air-tight space over the area of pathology, a unique opportunity exists to change the parameters of local environment, including the temperature, pressure, gas composition, etc. For example, the concentration of oxygen can be reduced through instilling some inert gas to suppress infectious processes. There exists the possibly to periodically or continuously introduce drugs on the top of a wound simultaneously with the irradiation, which permits the realisation of, for instance, a local photodynamic therapy technique to treat either malignant or non-malignant ailments, in the latter case by dint of utilising the accompanying bactericidal effect. The closed air-tight space can be realised with the help of placing a hood transparent for the radiation, in which it is possible to create, for example, air rarefaction, as it has been actualised in vacuum-therapy. One of promising applications of this combined photovacuum therapy is to treat men's impotence. There is also a module to measure the bioobject's temperature to realise combined photo-hyperaemia or crio-therapy.

In order to realise combined photodrug therapy besides the forced introducing of drugs into the pathological zone, it is practicable to place a thin strip or gauze suffused with a drug, for instance, with photogem or photosens, immediately on the bioobject's surface. This is important while treating various oncological and dermatological diseases. This strip, made of thin elastic material, can wrap the pathological area tightly, for example a limb, which allows one to realise a unique combined method of photomechanical therapy of oedemas. In the case of employing super-miniature light diodes with a relatively low electrical power consumption, it is feasible to use a compact power supply unit placed right on the substrate. Thanks to this, it is possible to realise a unique method of treating, for instance, varicose veins by dint of compact and light device attached immediately on the patient's leg that will make it possible for the patient to move freely, for example, in the out-patient or home conditions under the doctor's supervision.

Thus, in general, a quite universal combined phototherapeutic device is suggested, which alloys many unique peculiarities and this permits increasing the effectiveness of light-treatment with respect to a number of severe diseases, which has never previously been possible to realise.

BRIEF DESCRIPTION OF THE FIGURES OF DRAWINGS

FIG. 1 shows a general scheme of the device.

FIG. 2—an examples of photomatrix devices to irradiate different organs.

FIG. 2A is a front view of the substrate 15 of FIG. 2.

FIG. 3—a photomatrix for body's surface (<<photoplaster>>)).

Figure 4:
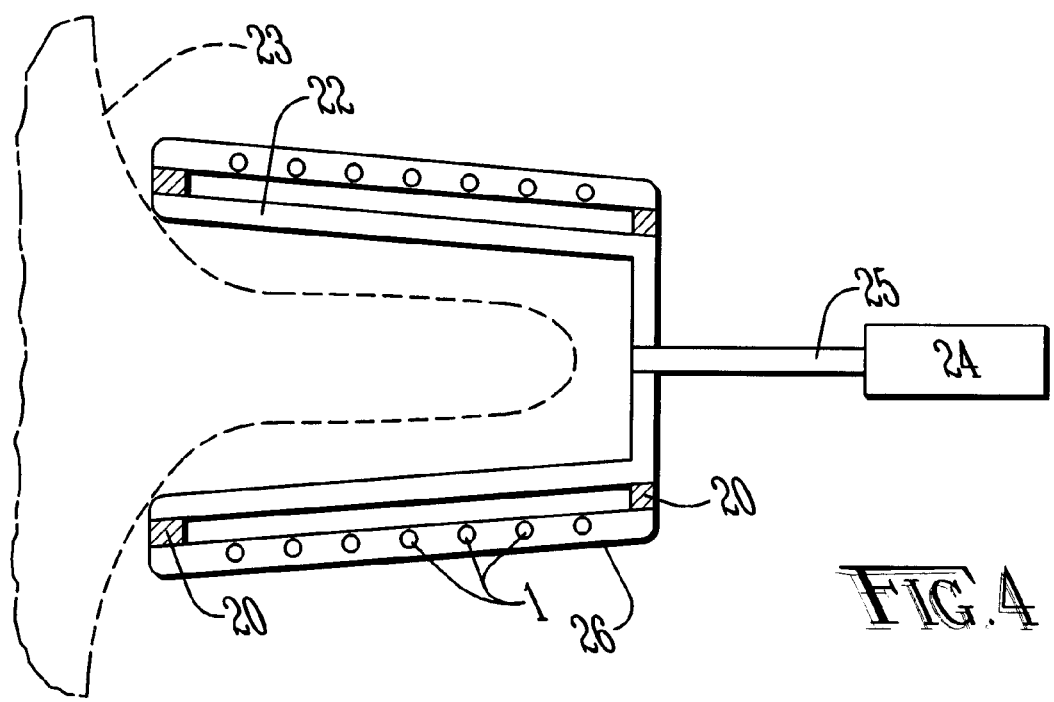

FIG. 4—photovacuum therapy with regard to urology.

FIG. 5—a laser system to irradiate extensive zones:
a) multi-fibre system;
b) single-fibre system.

FIG. 6 demonstrates a device operating on the basis of endoscopic irradiation of tube organs:
a) of a big diameter;
b) of a small diameter.

FIG. 7—the device to irradiate a hand:
a) palm <<laser (light) glove>>);
b) elbow bent.

Figure 8A:
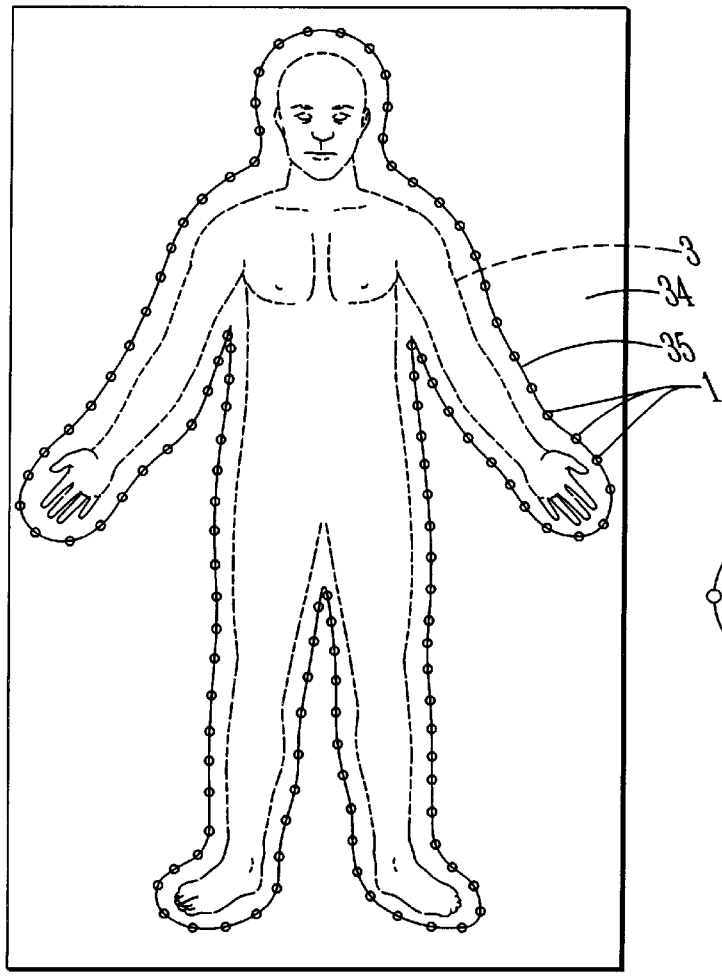
Figure 8B:
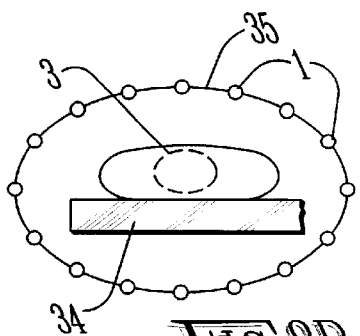

FIG. 8—the irradiation of the whole human being's body: light (laser) bath or shower:
a) in the semi-plane;
b) of the whole body.

FIG. 9 presents pulse photomatrix systems with solenoids of different shapes.
a) on the basis of Helmholtz coils;
b) separate element of a photomagnet system;
c) cylindrical geometry.

Figure 11A:
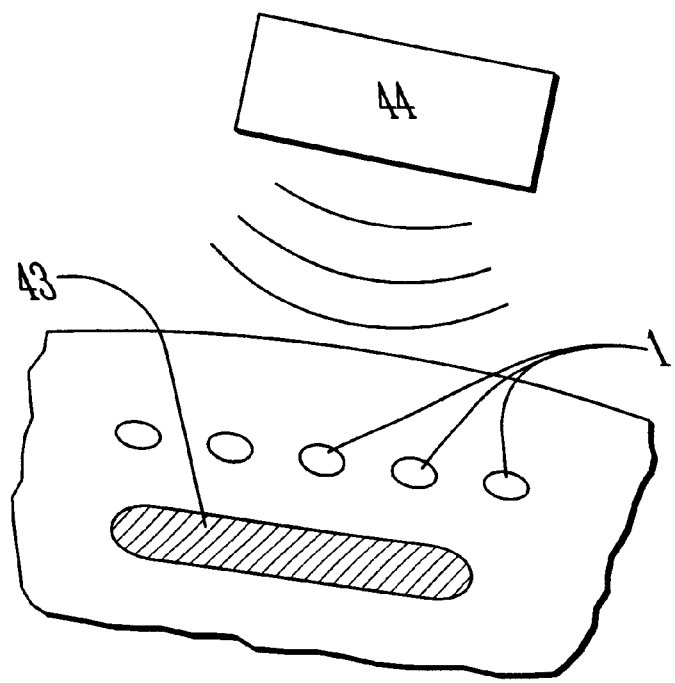

FIG. 10—Combined endoscopic system with distant power supply;

FIG. 11. Combined implantable system with distant power supply for:
a) photodynamic therapy;
b) electrooptical stimulation of the acoustic nerve.

Figure 12:
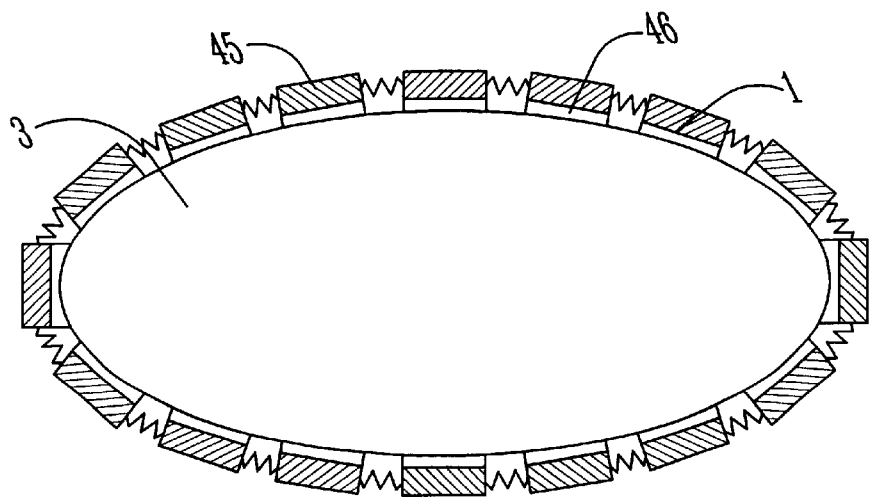

FIG. 12 presents a semi-rigid photomatrix system made of separate segments.

Figure 13:
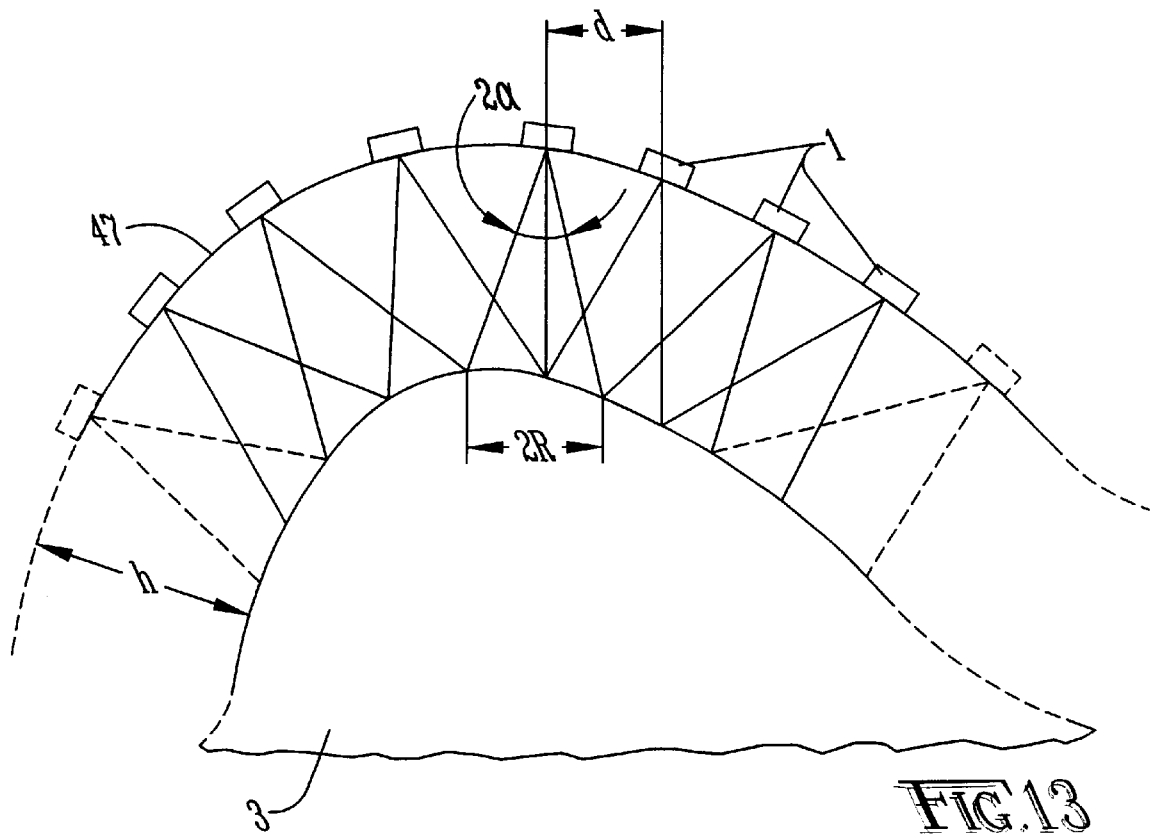

On FIG. 13—the principle of distribution of optical sources in space at irradiating complex surface.

WAYS OF REALISING THE INVENTION

The device presented in FIG. 1 works as follows. The sources of radiation 1 in form of light-diodes, according to the time mode of the control unit 2 (pulse or continuos), irradiate the bioobject 3, for example, a limb with the purpose of treating fracture, foot ulcer or skin pathologies. The bioobject 3 is simultaneously influenced, for instance, by pulse magnetic field that is regulated by the unit 4 (solenoids placed along the bioobject are not shown). In order to synchronise the influence with the organism's biorhythms, in particular with the patient's pulse, a photopletismographic sensor 5 is involved, the output signal of which is accepted by the commutation unit 6. This signal carries information about the patient's pulse and blood-filling capacity, which is used to handle the treatment process. In particular, after reaching the maximum of bloodflow and its subsequent reduction, the treatment process is terminated. The additional modules 7 together with the control units 8 are used to change the gas mixture and temperature in the space over the pathological area confined by the substrate 9 and flanges 10. The latter are also utilised to fix and stabilise the distance between the sources of radiation 1 and the bioobject's surface 3. The power supplies unit 11 serves to feed both the sources of radiation and additional physiotherapeutic modules.

In FIG. 2 the possible shapes of the substrates to irradiate various organs of the human being are presented. In particular, the mask 12 with the built-in sources of radiation 1 follows the shape of the bioobject (the face) and has been designed for cosmetological purposes to improve the blood microcirculation and metabolism of skin and to smooth wrinkles. The substrate 13 in form of a semi-sphere is employed to irradiate the head in both cosmetology to treat baldness and activate the brain bloodflow at rehabilitation of patients affected by insult or cerebral palsy. The substrate 14 in form of a headphone with built-in sources of radiation is utilised to treat the inflammatory ailments of the ear: otitis, neuritis of the acoustic nerve, etc. The substrate 15 by its form resembles dentures and is used to irradiate the whole mouth including the concavities near gums. The substrate 16 envelopes part of the neck and are employed to treat osteohondrosis and neuritis of the neck nerve. The substrate 17 traces the shape of the woman's breast and is used to treat inflammatory processes as well as to conduct photodynamic therapy of the mammary gland affected by the malignant tumour.

FIG. 3 shows the simplified construction of <<(photoplaster)>> in form of a substrate that repeats the shape of the bioobject 3 with a wound or furuncles. The thin bactericidal plaster or strip 18 suffused with a drug, in particular, photosensitizer used in photodynamic therapy is put over the wound. Then, the flexible substrate 19 with the built-in sources of radiation 1 is positioned on top. The stops 20 made of medical rubber serve to stabilise the distance between the sources of radiation, whereas the ordinary adhesive tape 21 serves to fix the photoplaster to the bioobject.

FIG. 4 demonstrates the combined device to realise photovacuum therapy. The vacuum-therapy technique has been employed in urology when treating impotence for a long time, the essence of which consists in putting cylindrical or conic hood 22 on the penis 23 and its squeezing to the body at the groin. Afterwards, rarefaction is created in the hood with the help of the pump 24 through the channel 25, under the influence of which the arterial bloodflow is increased and the products of the inflammatory process are removed out of the acinus channels. To additionally enhance the microcirculation in capillaries and to treat surface pathologies, the irradiation of external surface of the bioobject is carried out with the help of sources of radiation 1 built into the conic substrate 26. For more convenience, the stops 20 made of medical rubber stuck to the substrate and grasping it are introduced into the photomatrix system scheme.

FIG. 5a illustrates the matrix system, in which the distant ends of light-guides 27 serve as the sources of radiation, with the light-guides being collected into a single plait whose but-end is irradiated by the source of radiation 28. The ends of the light-guides are fixed to the substrate 29. In order to create a more uniform exposure of the bioobject 3, an additional strip 30 with partially mirror-like surfaces is introduced, in which the radiation is re-distributed over the bioobject's surface at the expense of re-reflection. Besides the substrate 29, the radiation can be introduced through the light-guide 27 (FIG. 5b) into the diffusive partially mirror-like strip 30, in which it also is re-distributed and elucidates various zones of the bioobject.

In the case of necessity the irradiation of inaccessible internal concavities, for example, the rectum, can be achieved utilising the cylindrical substrate 31 (FIG. 6a), in which the sources of radiation 1 are located on the external surface of the substrate flush with it. Irradiated concavities with relatively small diameter, for instance, the urethra 32, the sources of radiation can be placed in the central axial part of the cylindrical substrate made of optically transparent material (FIG. 6b).

Figure 7A:
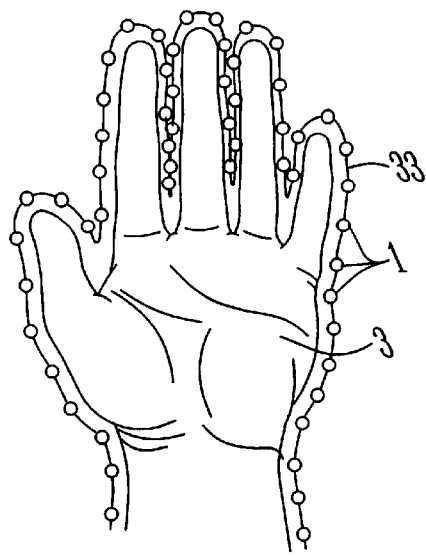
Figure 7B:
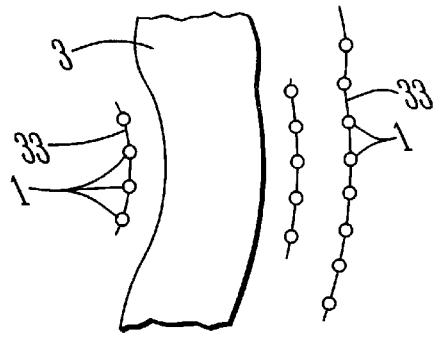

While treating various pathologies of the palm (dermatological ones or twisted wrists, fractures, oedemas, cuts, etc.), it is possible to utilise the substrate 33 that traces the shape of the palm and fingers (FIG. 7a). In this case, the sources of radiation 1 are located on the internal side of the substrate 33 in form of a glove (<<photoglove>>) grasping the bioobject's surface 3. It is also feasible to built microelectrostimulators into the substrate to treat neurologic diseases. When treating traumas of the elbow or knee bents (FIG. 7b), the substrate 33 is made in form of an elbow-cover or knee-cover, as it is used in some sports games, on the inner side of which the sources of radiation 1 are placed. In the latter case, it is practicable to employ a device that resembles a lamp reflector (dot line in FIG. 7b) on whose internal side the sources are positioned.

At irradiation the whole body (bioobject 3) (FIG. 8a), it is possible to use the construction of the substrate put on a coach 34 in form of an <<arch>> or <<knight armours>> 35, the inner side of which has a myriad of sources of radiation 1. A simpler solution consists in using separate sections in form of semi-cylinders with certain geometry where the sources of radiation are placed on their internal side. These semi-cylinders are put on an ordinary coach 34, on which a human body (bioobject 3) is positioned. Such photomatrixes are quite promising to treat extensive dermatological pathologies, for example, burns or ulcers, to conduct over-skin blood therapy, treatment of yellow jaundice using light diodes of the blue range of spectrum to destroy bilirubin in blood. Treated the infectious deseases of new-borns, the matrixes of the blue range can be put to the outside walls of ordinary incubators that are transparent for the radiation. Irradiated the patient on all sides simultaneously, for example, while treating burns or in general therapy (FIG. 8b), the patient is placed on a coach 34 transparent for the radiation or on a net such as a hammock, which in their turn are inserted inside the <<arch>> or <<knight armours>> 35 whose inner surface is strewn with the sources of radiation and repeats the shape of the human being's body.

FIG. 9 presents different variations of the combined photomagnetic system. In the case of a complex shape (FIG. 9a), the magnet modules 36 together with the separate sources of radiation 1, for instance, in form of Helmholtz coils (FIG. 9b) are located over the corresponding area of pathology, in particular, over the prostate gland. The influence on this gland is provided by both the matrix of infrared light diodes and by the pulse magnetic field induced by a pulse electric current flowing through separate solenoids (FIG. 9b) gathered into a matrix (FIG. 9a). When it is required that a limb (bioobject 3) (FIG. 9c) be treated, the pulse magnetic field, produced by modules 36 of solenoids, influences the pathological area, with the matrixes of the sources of radiation 1 being positioned between solenoids.

At endoscopic applications, separate sources of radiation are not placed on the internal side of the substrate, as it has been described earlier, for they are located on the external side of the substrate (FIG. 10). A cylindrical capsule 37 with the electrostimulator electrodes 38 and sources of radiation 1 on the on the outside is introduced into the bioobject, in particular, into the alimentary tract. An inductive coil 39 is built into the capsule, the capsule shell 40 being made of biologically inert material. A field magnet 41 is positioned on the external side of the bioobject and manages the location of the capsule 37, where in this case the magnet micromodules are built in. The source of the pulse magnetic field 42 serves to induce electromotive force in the coil 39 to feed the electrostimulator and the source of radiation operating in the time mode determined by the unit 42. The operational principle is quite simple. The capsule with a size of 6×15 mm can be swallowed by the patient and then after its natural passing through the stomach it can be fixed in a certain zone of the intestines determined with help ultrasonic diagnostics. Afterwards, the unit 42 is switched on and in accordance with a mode required it provides the combined electrooptical influence on the intestines walls. The capsule can also be inserted from the side of the rectum. This microcapsule can be a separate micromodule within an endoscopic microrobot designed to conduct diagnostic and treating procedures. Separate sources of radiation together with the micro-inductors collected into a matrix allow the irradiation of pathological zones without using accumulators and corresponding electrical wires. This allows one to place a compact photomatrix, for example under a bandage or into the mouth.

Figure 11B:
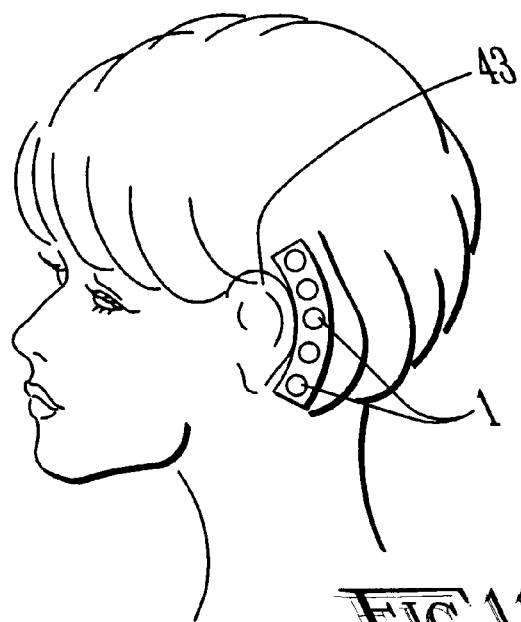

FIG. 11 presents schemes of implanting the device suggested. In the case of malignant pathology with inner localisation 43, the matrix of sources of radiation is implanted near the pathological zone, with their power supply being provided with the help of the external unit 44. This scheme is encouraging for the realisation of photodynamic therapy of cancer when the radiation emitting from ordinary sources of radiation using light-guides is improbable to non-invasively irradiate the malignant pathology that contains photosensitizers. This is typical, for example, for the mammary and thyroid cancer. The sizes of the sources of radiation are about Ø3 mm×1 mm, which makes it practicable to implant them into the human being's organism. FIG. 11b illustrates the placing of the sources of radiation implanted in various zones of the ear with the purpose of combined electrostimulation of the acoustic nerve to treat, particularly, neuritis.

FIG. 12 gives an example of the photomatrix system, the substrate of which consists of separate segments. The bioobject's surface 3 in this model is grasped by separate segments 45 whose shape is, for instance, rectangular. Within each segment, the sources of radiation 1, for example light diodes, are uniformly strewn. The segment can be made in form of a monolithic integrated chip with the soldered-in hybrid light-diode crystallines covered by the substrate 46 transparent for the radiation that simultaneously plays the role of a stop, providing the mean distance between the surfaces of the bioobject and light diodes. The separate segments are attached to each other by a flexible spring-like bond. FIG. 12 shows the cross section of the construction. In the other direction, the segments can have a large dimension and in its turn they can be split into dividable sections. Such a construction can be utilised to irradiate limbs, the neck as well as to cover the whole body near the stomach, lungs or sex organs.

FIG. 13 presents the generalised scheme that explains the principle of constructing and the methods of calculation with respect to the photomatrix systems mentioned above. The bioobject 3 with a complex shape is grasped by the substrate 47, on which the sources of radiation 1 are placed, in particular, the light diodes. The conditional signs: h—the mean distance between the surfaces of the substrate and bioobject, d—the distance between the neighbouring sources of radiation, R—the radius of the light spot on the bioobject's surface, α—the half-angle of the radiation divergence from the source of radiation. The estimated basic parameters can approximately be derived from the expressions (1)–(3). For example, to reach a flux of I=100 mW/cm² on the bioobject's surface, which is indispensable for photodynamic therapy, when the single light diode power is P=10 mW at the irradiation of dermatological pathology with the overall square 400 cm² in accordance with the expression (3) for τ≈1, it is necessary to employ 4,000 light diodes or 10 light diodes per 1 cm² of the substrate. Changing the indicatrix of the light diodes' irradiation with the help of optical systems, one can regulate the size of the light spots on the bioobject produced by a separate light diode as well as the degree of their overlapping. In order to create a uniform exposure, the light beams should at least touch each other, i.e., in this case k=1 and the expression (2) gives the following d≅2R. To create a more uniform exposure, it is required to provide a more intense overlapping of the beams (k>2), which can be attained through increasing the angle α and reducing the distance between the sources of radiation d. This leads to the decrease in the required power for each light diode with the simultaneous increase in the total amount of the sources of radiation.

Examples of concrete realisations of the device.

THE BEST VARIATION

Photomatrix device to treat various pathologies of limbs: bruises, fractures, burns, oedemas, infectious wounds, ulcers of different origin, arthritis, dermatological pathologies including skin cancer, psoriasis, keloids, etc. as well as to realise photodynamic therapy on the basis of photosensitizers with regard to both oncological and non-oncological ailments. The geometric form of the device: an oblong hollow cylinder with the light diodes placed on the inner side, with the output windows turned inside the cylinder. The form of the internal surface depends on the bioobject's shape and can be close to cylindrical, conic or their combination. There is an example of the cylindrical section to treat post-mastectomical oedemas of the woman's hand after the radical operation in respect to mammary cancer. This section has the diameter of 200 mm, length 300 mm and was made of plastic and consists of two parts that can open to ease fixation on the patient's hand. The 240 <<Kirhbright>> light diode sources of radiation are placed on the inner side of the cylinder; the mean distance between separate sources of radiation is 30 mm. The wavelength is 0.67 μm. The power of each source of radiation in the continuous mode is 5 mW, the average flux on the bioobject's surface being around 1 mW/cm². The light diodes are connected sequently-parallelly. The power supply is provided from the outlet with 220 V and 50 Hz. Two rubber rings 5 cm in diam connected with the cylinder surface by dint of three springs placed to each other at an angle of 120° are placed at the butt-ends of the photomatrix system. The patient's hand is sequentially introduced into the two rubber rings and is fixed at the axis of the cylinder by means of the springs. The total weight of the cylinder is not more that 0.5 kg, which allows the patient to be in the vertical position and to easily endure the load of the device described. The duration of the therapeutic procedure is 30 min. The number of procedures is 10 undergone in the course of 10 days.

If there is a possibility to touch the device presented by the hand's surface, it is possible to realise this device in form of several flat segments of rectangular form with a dimension of 15×60 mm. To provide a uniform grasping of the hand at the wrist, the section should involve approximately 9–12 segments, connected by a flexible bond (FIG. 12). One of such sections can be used to conduct therapy of blood and treatment of local pathologies. In the case of treatment a more extensive pathology, one can utilise up to 4–5 sections of that kind. It is feasible to locate up to 10 light diodes within one segment in two rows with five light diodes in each row.

Photoplaster to irradiate the elbow bent with a hit trauma. The form of the photomatrix is close to the semi-sphere with a radius of 50 mm. The wavelength of the red light diodes is 0.63 μm and of the infrared ones is 0.85 μm. The power of radiation is about 10 mW at the wavelength of 0.63 μm and 0.3 W at the wavelength of 0.85 μm. The number of light diodes is 88. The source of radiation is built into the elbow-cover used by volleyball-players and is fixed with the help of elastic fabric. The power supply is autonomous by dint of two <<Krona>> batteries. One light-therapy procedure lasts for 15 min. The total number of procedures is six, within one week.

Magnet-laser device to treat chronic prostatitis. As the sources of radiation, semiconductor GaAs lasers with a wavelength of 0.89 μm, peak power of 5 W, pulse duration of 10(−7) s and repetition rate of 800 Hz are utilised. In the simplest case, one can use one laser placed in the centre of the solenoid in form of a Helmholtz coil with a diameter of 10 cm. This module can be employed autonomously, for instance, to treat nervous-muscular pathologies as well as prostatitis. To irradiate internal organs, in force of scattering, it is necessary to use 9 sources of radiation, one of which is positioned in the centre and the rest 8 are placed uniformly on a circle. The magnitude of pulse magnetic field induction at the surface is around 1 Tesla, pulse duration near 1 ms. Six solenoids are uniformly placed over the body around the prostate gland and fixed by a belt. One procedure takes 20 min. The total number of procedures is six; the patient should undergo them every other day.

The device with a remote power supply. In the capacity of a source of radiation, a compact light diode with a size of 3×3 mm is used (Plant <<Start>>, Moscow), its wavelength is 0.65 μm, power 0.5 mW, internal resistance 150 Ohm, feeding current 5 mA. The unit of external power supply is made as a flat solenoid forming pulse magnetic field with a tension of 0.4 Tesla and duration of 1 ms. In a compact inductive coil, this field induces an electromotive force of 10 V, which in a closed circuit with the load in form of a light diode provides the flowing of a current of nearly 12 mA, which is quite enough to feed the light diodes. The light diodes together with the inductive coils of a size of Ø3 mm×5 mm are placed on the matrix's surface used to irradiate the mouth (FIG. 2, position 6). The number of light diodes is 16. Application: the treatment of inflammatory processes in the mouth.

As the sources of radiation, practically any sources of radiation can be utilised in this invention, which have already been employed in phototherapy, for instance, various types of lasers, light diodes, incandescent lamps with light filters, gas discharge and luminescent lamps (neon, xenon, mercury etc.) etc. In the latter case the dimensions of gas discharge elements should be minimised. In the case of irradiating the bioobject in form of close to a cylinder, for example, limbs, the gas discharge flasks can be made as a thin cylinders placed uniformly around the limbs, with their axises being parallel to the averaged axis of the limb. The mirror-like surface of the substrate can grasp all this sources of radiation, i.e., the construction of the emitter should resemble the constructions of the pumping sources of laser systems but the limb is placed in centre instead of the active element of the laser. Depending on the medical task, the sources of radiation can operate in different modes and diverse spectrum ranges predominantly from 0.2 to 3 μm with various monochromatic degrees from $10^{-3}$ to $10^3$ nm.

What is claimed is:

1. A photomatrix device for the combined therapeutic treatment of a pathological zone of a patient's body, said pathological zone having an extended complex geometric shape, comprising:

a plurality of radiation sources emitting radiation of one or more wavelengths in the range from ultraviolet to radio and fixed on a substrate to envelope said pathological zone, wherein said substrate has a shape conforming to said extended complex geometric shape of said pathological zone, a plurality of stops between said pathological zone and said substrate to establish the distance between said pathological zone and said substrate, a plurality of physiotherapeutic modules, a control unit and a power supply unit operatively connected to said radiation sources and said physiotherapeutic modules, and a commutation unit operatively connected to said control unit to provide modes of operation in accordance with a given program of operation, wherein the indicatrixes of radiation from said radiation sources and the positions on said substrate of said radiation sources provide a required distribution of radiation intensity on said pathological zone and further wherein said wavelengths of said radiation sources are selected to concur with the maximums of the bioaction spectrum or the bands of absorption of biomolecules of both exogenous and endogenous origin including drug compounds and photosensitizers; and wherein said radiation sources are placed uniformly over said substrate and wherein the number N, power P and the distance d between said radiation sources are approximately determined by the following system of interconnected expressions:

$$P \approx \frac{I\pi R^2}{k}; \quad (1)$$

$$d \leq \frac{2R}{k}; \quad (2)$$

$$N \geq \frac{IS}{P\tau}, \quad (3)$$

where I is the light intensity on the surface of said pathological zone; S is the overall area of the exposed pathological zone; R is the mean radius of the light spot produced by a single radiation source as determined by the equation $R = h \cdot tg\alpha$, where h is the average distance between the surfaces of said substrate and said pathological zone; $\alpha$ is the half-angle of radiation divergence; $\tau$ is the radiation loss from said radiation sources to said pathological zone ($0 \leq \tau \leq 1$); and k is the ratio taking into account the degree of light beams' overlapping on the surface of said pathological zone ($1 \leq k \leq N$).

2. The device of claim 1, wherein said substrate comprises separate rigid segments, wherein said separate segments are fixed in space independently as anglepoise hands.

3. The device of claim 1, wherein said substrate comprises separate semi-rigid segments, wherein said separate segments are fixed in space independently as anglepoise hands.

4. The device of claim 1 wherein said substrate comprises separate rigid segments and further wherein said separate rigid segments are connected with each other by bonding means so that said substrate may be adapted to conform to said pathological zone by changing the size of said separate rigid segments or the angle or distance between said separate rigid segments.

5. The device of claim 1, wherein said radiation sources are placed on an external side of said substrate and further wherein said radiation is emitted through holes in said substrate.

6. The device of claim 5, wherein said holes further comprise lenses.

7. The device of claim 5, wherein said holes further comprise output windows.

8. The device of claim 1, wherein said radiation sources further comprise light guides fixed in said substrate and coupled to one or more radiation emitters.

9. The device of claim 1, wherein said radiation sources further comprise a plurality of optical beam splitters coupled to one or more radiation emitters.

10. The device of claim 1, further comprising optical elements between said radiation sources and said pathological zone.

11. The device of claim 10, wherein said optical elements comprise a protective transparent plate.

12. The device of claim 10, wherein said optical elements comprise a low absorption diffuse screen.

13. The device of claim 10, wherein said optical elements comprise a positive lens associated with each of said radiation source.

14. The device of claim 10, wherein said optical elements comprise a negative lens associated with each of said radiation sources.

15. The device of claim 1, wherein said substrate comprises a mirror-like surface between said radiation sources.

16. The device of claim 1, wherein said radiation sources comprise semiconductor hybrid lasers operating in a continuous mode.

17. The device of claim 1, wherein said radiation sources comprise semiconductor hybrid lasers operating in a pulse mode at a repetition frequency of 1 to $10^4$ Hz and a pulse duration of 0.1 to $10^{-9}$ s.

18. The device of claim 1, wherein said radiation sources comprise wide-band hybrid light emitting diodes having a spectrum width up to 0.3 $\mu$m and narrow-band hybrid light emitting diodes emitting in the range of 200 to 2,000 nm with a width of the radiation line from 5 to 40 nm, a power of radiation from 0.1 mW to 1 W and a radiation indicatrix from 10° to 180°.

19. The device of claim 1, wherein said radiation sources comprise chemical substances placed into confined optically transparent concavities on said substrate wherein radiation is emitted as a result of chemical reactions in said chemical substances.

20. The device of claim 1, wherein said radiation sources comprise optical elements generating secondary emitted radiation from primary sources as a result of non-linear effects in said optical elements.

21. The device of claim 1, wherein said radiation sources comprise optical elements generating secondary emitted radiation from primary sources as a result of fluorescence.

22. The device of claim 1, wherein said substrate extends beyond said pathological zone to adjacent areas of the patient's body.

23. The device of claim 1, wherein said radiation sources are selected to emit radiation of a wavelength which activates a mixture of photosensitizers.

24. The device of claim 1, wherein said radiation sources comprise high-power radiation sources emitting in the visible and infrared ranges for simultaneous phototherapy and thermal therapy.

25. The device of claim 1, wherein said physiotherapeutic modules comprise at least one magnetotherapy module.

26. The device of claim 25, wherein said magnetotherapy module comprises a built-in optical source.

27. The device of claim 26, wherein said magnetotherapy module comprises a matrix grasping said pathological zone, said matrix comprising flat sources of a magnetic field having a magnetic field strength from $10^{-4}$ to 10 Tesla.

28. The device of claim 25, wherein said magnetotherapy module comprises a plurality of solenoids having axes placed parallel to a surface of said pathological zone and a plurality of optical sources placed between said solenoids, said solenoids producing a magnetic field having a magnetic field strength of $10^{-4}$ to 10 Tesla.

29. The device of claim 1, wherein said physiotherapeutic modules comprise an electrostimulator having two or more electrodes contacting the pathological zone.

30. The device of claim 1, wherein said physiotherapeutic modules comprise sources of acoustic vibrations.

31. The device of claim 30, wherein a physiological solution is interposed between said sources of acoustic vibration and said pathological zone and further wherein said solution comprises a drug and a photosensitizer for combined photosonodynamic therapy.

32. The device of claim 1, wherein said substrate further comprises side flanges with resilient air-tight edges bordering the pathological zone.

33. The device of claim 32 further comprising means for adjusting the temperature, pressure and composition in the environment over said pathological zone.

34. The device of claim 1, wherein said physiotherapeutic modules comprise a plurality of cryotherapy modules.

35. The device of claim 34, further comprising at least one module for introducing drugs, chemicals or biological molecules to said pathological zone.

36. The device of claim 1, further comprising a transparent hood between said substrate and said pathological area, said transparent hood having edges adjoining said pathological zone and further comprising a matrix of radiation sources positioned on said transparent hood.

37. The device of claim 36, wherein said transparent hood is connected through a hose with a module adjusting the pressure in the space under said transparent hood.

38. The device of claim 32 wherein said transparent hood comprises a cylinder having a closed end.

39. The device of claim 32, wherein said transparent hood comprises a semi-sphere.

40. The device of claim 32, wherein said transparent hood comprises a truncated cone.

41. The device of claim 1, further comprising a flexible elastic strip between said substrate and said pathological zone, said flexible elastic strip tightly grasping said pathological zone and said flexible elastic strip further being at least partially transparent to said radiation.

42. The device of claim 41, wherein said flexible elastic strip further comprises a drug preparation, including photosensitizers.

43. The device of claim 1, further comprising a closed capsule having walls transparent to said radiation and enclosing said control unit, said power supply unit, said commutation unit, said therapeutic modules and said radiation sources.

44. The device of claim 43, further comprising a microstimulator with electrodes fixed on an external surface of said closed capsule, said closed capsule having means for affixing said closed capsule to the patient's body and means for regulating the position of said closed capsule.

45. The device of claim 44, wherein said means for regulating the position of said closed capsule comprises a thread having means for supplying electrical power to said capsule and means for disconnection from said closed capsule.

46. The device of claim 1, wherein said power supply comprises one or more inductor coils electrically connected to said radiation sources and said therapeutic modules and an external pulse electromagnetic magnetic device for inducing an electrical current in said one or more inductor coils.

47. The device of claim 46, further comprising at least one electrostimulator and wherein said radiation sources comprise super-miniature radiation sources whereby said super-miniature radiation sources, said at least one electrostimulator and said inductor coils may be placed into an inner zone of the patient's body.

48. The device of claim 1, wherein said radiation sources comprise a chemical substance, uniformly spread over the pathological zone, said chemical substance being capable of fluorescence under the action of external physical factors.

49. The device of claim 1, wherein said substrate comprises a hollow cylinder.

50. The device of claim 1, wherein said substrate comprises a hollow semi-cylinder.

51. The device of claim 1, wherein said substrate comprises a hollow semi-sphere.

52. The device of claim 51 wherein said substrate is transparent and said radiation sources are located on an exterior surface of said substrate.

53. The device of claim 1, wherein said substrate comprises a flexible glove.

54. The device of claim 53 further comprising at least one electrostimulator having electrodes in contact with the skin of the patient's fingers.

55. The device of claim 1, further comprising a cooling system for cooling said radiation sources.

56. The device of claim 1, further comprising a feedback channel comprising one or more biosensors adapted to be attached to the pathological zone and operatively connected to said control unit.

57. The device of claim 1 further comprising artificial teeth wherein said radiation sources are built into said artificial teeth.

58. The device of claim 1, wherein said substrate comprises a mask that is adapted to grasp the face of the patient.

59. The device of claim 58 further comprising at least one magnet and at least one electrostimulator.

60. The device of claim 1, wherein said pathological zone is a zone of adipose tissue accumulation with said wavelength of said radiation being chosen to maximize activation of photochemical, photothermal, photoacoustic, or photodynamic processes to remove adipose tissue and to activate the production of biologically active substances responsible for weight regulation and further comprising at least one photosensitizer introduced to said pathological zone.

61. The device of claim 60, wherein said physiotherapy modules further comprise electrostimulation, ultrasonic and vacuum therapy modules.

62. The device of claim 1, wherein said substrate comprises a bracelet grasping the wrist of the patient.

63. The device of claim 1, further comprising a timer operatively connected to said control unit for switching said radiation sources in accordance with the patient's biological rhythms.

64. The device of claim 1, wherein said radiation sources are adapted to uniformly grasp the zones of the patient's body responsible for immune system function and said wavelength of said radiation sources is selected from the red or infrared spectra at a flux of 2 to 200 $mW/cm^2$ and a time of exposure of 10 to 50 min. so as to alter the patient's immune activity through converting antibodies from the non-active into the active form.

65. The device of claim 1, wherein said substrate comprises a flexible fillet adapted to uniformly grasping the patient's body in the area of the lungs and further wherein said wavelength of said radiation is in the range of the greatest transparency of biotissue.

66. The device of claim 65 further comprising means for administration of drugs or photosensitizers.

67. The device of claim 1, wherein said substrate comprises transparent walls of an incubator for new-born children and further wherein said radiation sources comprise blue light diodes.

68. The device of claim 1, further comprising mechanical needles from 5 to 10 μm in length uniformly strewn over the substrate, said needles being in contact with said pathological zone, said substrate further comprising means for pressing said needles into said pathological zone.

69. The device of claim 68, wherein said physiotherapy modules comprise at least one ultrasound module.

70. The device of claim 1, wherein said physiotherapy modules comprise at least one electrophoresis module.

71. The device of claim 1, wherein said required distribution of radiation intensity is further provided by means of a special distribution of the power applied to said radiation sources.

72. The device of claim 1, wherein said required distribution of radiation intensity is further provided by means of a special distribution of masks positioned between said radiation sources and said pathological zone.

73. The device of claim 1, wherein said required distribution of radiation intensity is further provided by means of a special distribution of filters positioned between said radiation sources and said pathological zone.

74. The device of claim 1, wherein said substrate is affixed to objects adjoining the patient's body, and further wherein said objects are selected from the group consisting of the patient's clothing, a pillow, a blanket, a bedsheet, a veil, the back of a chair, the back of an armchair, a bed, a mattress, and a sofa.

75. The device of claim 74, wherein said substrate further comprises biologically active agents.

76. The device of claim 75, wherein a volume is defined between said substrate and said pathological zone and said volume is transparent to said radiation.

77. The device of claim 1, wherein said pathological zone is located in an internal cavity of the patient's body and said substrate conforms to said internal cavity.

78. The device of claim 1 wherein said radiation sources comprise compact lamps with light filters.

79. The device of claim 1, wherein said substrate further comprises a plurality of cooling systems.

80. The device of claim 79, wherein said cooling systems are in contact with the skin of the patient.

* * * * *